United States Patent [19]
Pike et al.

[11] Patent Number: 5,340,586
[45] Date of Patent: * Aug. 23, 1994

[54] METHODS AND FORMULATIONS FOR USE IN TREATING OOPHORECTOMIZED WOMEN

[75] Inventors: Malcolm C. Pike, Long Beach; Darcy V. Spicer, Pasadena, both of Calif.

[73] Assignee: University of Southern California, Los Angeles, Calif.

[ * ] Notice: The portion of the term of this patent subsequent to May 18, 2010 has been disclaimed.

[21] Appl. No.: 62,886

[22] Filed: May 17, 1993

Related U.S. Application Data

[63] Continuation-in-part of Ser. No. 952,513, Feb. 3, 1993, which is a continuation-in-part of Ser. No. 684,612, Apr. 12, 1991, Pat. No. 5,211,952.

[51] Int. Cl.$^5$ .......................... A61K 9/50; A61K 9/14
[52] U.S. Cl. .................................... 424/426; 424/485; 424/486; 424/433
[58] Field of Search ............... 424/422, 423, 424, 426, 424/430, 432, 433, 484, 485, 486, 487, 488, 489, 490, 496, 497, DIG. 14; 514/2, 12, 21, 800, 841, 842, 843; 530/313, 850, 853; 128/830, 832, 833

[56] References Cited

U.S. PATENT DOCUMENTS

| | | | |
|---|---|---|---|
| 3,731,683 | 5/1973 | Zaffaroni | 424/434 |
| 3,797,494 | 3/1974 | Zaffaroni | 424/434 |
| 4,264,575 | 4/1981 | Zimmerman et al. | 424/432 |
| 4,336,243 | 6/1982 | Sanvordeker et al. | 424/449 |
| 4,762,717 | 8/1988 | Crowley, Jr. | 424/425 |
| 5,211,952 | 5/1993 | Spicer et al. | 424/426 |

OTHER PUBLICATIONS

Watts et al, "Effects of Oral Estrogens and Esterified Estrogens +Androgen on Bone Mineral Density in Post-Menopausal Women", *The 2nd Annual Meeting North American Menopause Society Programe*, S-F16, Sep. 25-28, 1991.

Bergkvist et al., "The Risk of Breast Cancer After Estrogen and Estrogen-Progestin Replacement", *N.E.J. of Med.*, 321: 5, pp. 293–297 (Aug. 3, 1989).

Burger et al., "The Management of Persistent Menopausal Symptoms with Oestradiol-Testosterone Implants: Clinical, Lipid and Hormonal Results", *Maturitas*, 6: 351–358 (1984).

Chetkowski et al., "Biologic Effects of Transdermal Estradiol", *N.E.J. of Med.*, 314: 5, pp. 1615–1620 (Jun. 19, 1986).

Conn et al., "Gonadotropin-Releasing Hormone and its Analogues", *N.E.J. of Med.*, 324: 2, pp. 93–103 (Jan. 10, 1991).

Cowsar et al., "Biodegradable and Nonbiodegradable Fibrous Delivery Systems", *Long Acting Contraceptive Delivery Systems* pp. 145–162 (eds. Zatuchni et al. 1984).

Diczfalusy et al., "Some Pharmacokinetic and Pharmacodynamic Properties of Vaginal Delivery Systems That Release Small Amounts of Progestogens at a Near Zero-Order Rate", *Long-Acting Contraceptive Delivery Systems*, pp. 213–227 (eds. Zatuchni et al. 1984).

Donnez et al., "Treatment of Uterine Fibroids with Implants of Gonadotropin-releasing Hormone Agonist: Assessment by Hysterography", *Fertility and Sterility*, 51: 6, pp. 947–950 (Jun. 1989).

(List continued on next page.)

Primary Examiner—Thurman K. Page
Assistant Examiner—Carlos Azpuru
Attorney, Agent, or Firm—Robbins, Berliner & Carson

[57] ABSTRACT

Compositions and methods which are effective to prevent symptoms of loss of ovarian function (e.g., in oophorectomized women) over a period of time are described, consisting essentially of an effective amount of an estrogenic composition and an effective amount of an androgenic composition. The levels of estrogens and androgens employed are sufficient to reduce bone mineral density loss and minimize other side effects observed after oophorectomy, and at such low doses as to minimize any adverse impact on the patient's long-term prognosis or (in the case of testosterone) result in additional side effects.

14 Claims, No Drawings

OTHER PUBLICATIONS

Farish et al., "The Effects of Hormone Implants on Serum Lipoproteins and Steroid Hormones in Bilaterally Oophorectomised Women", *Act Endocrinologica*, 106:116–120 (1984).

Ferguson et al., "Compudose: An Implant System for Growth Promoting and Feed Efficiency in Cattle", *J. of Controlled Release*, 8:45–54 (1988).

George et al., *Int. J. Fertil.*, 34: 19–24 (1989).

Garza-Flores et al., "Development of a Low-Dose Monthly Injectable Contraceptive" *Contraception* 30: 79 (1984).

Gennant et al., "Quantitative Computed Tomography of Vertebral Spongiosa: A Sensitive Method for Detecting Early Bone Loss After Oophorectomy", *Annals of Internal Medicine*, 97: 5, pp. 699–705 (Nov. 1982).

Mertola et al., "Successful Treatment of Severe Premenstrual Syndrome by Combined Use of Gonadotropin-Releasing Hormone Agonist and Estrogen/Progestin", *J. of Clin. Endocrinology and Metabolism*, pp. 252A–252F (1991).

Lobo et al., "Subdermal Estradiol Pellets Following Hysterectomy and Oophorectomy", *Amer. Journal of Obstetrics & Gyn.* 138: 714–719 (1980).

Nezhat et al., "Estradiol Implants for Conception Control", *Amer. Journal of Obstetrics & Gyn.* 138: 1151–1156 (1980).

Notelovitz et al., "Influence of Extended Treatment With Oral Estrogens/Androgen Combination on Lipids and Lipoproteins in Surgically Menopausal Women", *North American Menopause Society, 1991 Meeting Abstract*, S–B5 (Montreal Canada 1991).

Nuwayser et al., "Microencapsulation of Contraceptive Steroids", *Long-Acting Contraceptive Delivery Systems*, pp. 65–75 (eds. Zatuchni et al. 1984).

Pike et al., "LHRH Agonists and the Prevention of Breast and Ovarian Cancer", *Br. J. Cancer*, 60: 142–148 (1989).

Pitt et al., "Capronor—A Biodegradable Delivery System for Levonorgestrel", *Long-Acting Contraceptive Delivery Systems*, pp. 48–63 (eds. Zatuchni et al. 1984).

Ralston et al., "Effect of Subdermal Oestrogen and Oestrogen/Testosterone Implants on Calcium and Phosphorus Homeostasis After Oophorectomy", *Maturitas.*, 6: 341–344 (1984).

Roy et al., "Vaginal Ring Clinical Studies: Update", *Long-Acting Contraceptive Delivery Systems*, pp. 581–594 (eds. Zatuchni et al. 1984).

Sandow et al., "Clinical Pharmacokinetics of LHRH Analogues", *LHRH Analogues in Gynaecology*, pp. 17–31.

Sherwin et al., "Postmenopausal Estrogen and Androgen Replacement and Lipoprotein Lipid Concentrations", *Am. J. Obstet. Gynecol.*, 156: 414–419 (1987).

Stanczyk et al., "A Randomized Comparison of Nonoral Estradiol Delivery in Postmenopausal Women", *Am. J. Obstet. Gynecol.* 159: 6, pp. 1540–1546 (Dec. 1988).

Urman et al., "Elevated Serum Testosterone, Hirsutism, and Virilism Associated With Combined Androgen-Estrogen Hormone Replacement Therapy", *Obstetrics & Gynecology* 77: 4, pp. 595–598 (Apr. 1991).

Youngs et al., "Effects of an Oral Estrogen-Androgen Preparation on Lipoprotein Lipids in Postmenopausal Women: a Pilot Study", *North American Menopause Society 1991 Meeting Abstract*, P–130 (Montreal Canada 1991).

Zorn et al., "Treatment of Endometriosis with a Delayed Release Preparation of the Agonist D-Trp$^8$-luteinizing Hormone-releasing Hormone: Long-term Follow-up in a Series of 50 Patients", *Fertility & Sterility*, 53: 3, pp. 401–406 (Mar. 1990).

Gilley et al., "Development of Controlled-Release Progesterone Microcapsules for the Regulation of Fertility During Lactation", *Southern Research Inst.* 73–74.

Kaufman, M. et al., *J. Clin. Oncol.*, y: 1113–19 (1989).

Hahn, et al., "Development of Microencapsulated Norgestimate as a Long-Acting Contraceptive", *Long-Acting Contraceptive Delivery Systems*, pp. 97–112 (eds. Zatuchni et al., 1984).

Hsieh et al., "Subecutaneous Controlled Administration of Estradiol From Compudose Implants: In Vitro and In Vivo Evaluations", *Rutgers University*, pp. 134–135.

Hsieh et al., "Enhanced Release of Drugs From Silicone Elastomers (I) Release Kinetics of Pineal and Steroidal Hormones", *RVG Development and Industrial Pharmacy*, 11(6&7) 1391–1410 (1985).

Jackanicz, Theordore M., "Vaginal Ring Steroid-Releasing Systems", *Long-Acting Contraceptive Delivery Systems*, pp. 200–211 (eds. Zatuchni et al., 1984).

Lewis et al., "Polymeric Considerations in the Design of Microencapsulation of Contraceptive Steroids", *Long-Acting Contraceptive Delivery Systems*, pp. 76–95 (eds. Zatuchni et al., 1984).

Lewis, Danny H., "Controlled Release of Bioactive Agents from Lactide/Glycolide Polymers", *Stolle Research and Development Corporation*, pp. 1–43.

METHODS AND FORMULATIONS FOR USE IN TREATING OOPHORECTOMIZED WOMEN

This application is a continuation-in-part of Ser. No. 07/952,513 filed Dec. 3, 1992, which in turn is a continuation-in-part of Ser. No. 07/684,612 filed Apr. 12, 1991 now U.S. Pat. No. 5,211,952.

BACKGROUND OF THE INVENTION

This invention relates to methods for treating oophorectomized women or women with other forms of ovarian failure, as well as to formulations for use in such methods. More particularly, the present invention is directed to methods and preparations effective for extended periods of time in preventing adverse symptoms associated with the loss of ovarian function in oophorectomized women or women with other forms of ovarian failure.

Oophorectomy and salpingo-oophorectomy are frequently performed in the United States, alone or with a hysterectomy. The most common indication is the treatment of uterine fibroids; other indications include malignancy and other benign gynecological disorders. In 1984, there were 498,000 such procedures performed in the U.S. As a consequence of oophorectomy, there is a marked reduction in serum estradiol and serum testosterone levels. Common side effects reported to occur as a result of these reductions in serum hormone levels after oophorectomy include: hot flashes, vaginal dryness and bone loss. Additional side effects that have been reported in some patients include: sweating, headache, depression, lability in mood, nausea and/or vomiting, nervousness, insomnia, pollakisuria, weight gain, sleepiness, dizziness, decreased libido and mild breast tenderness or swelling.

Current standard treatment of oophorectomized women calls for administration of an estrogen, or an estrogen and an androgen. Typical treatment protocols have involved the administration of: an oral estrogen alone (such as conjugated estrogens or esterified estrogens) or with an oral androgen (such as methyltestosterone); transdermal estrogen (such as estradiol); and injectable pellets of estrogen alone, or with testosterone [Stanczyk, F. Z. et al., "A randomized comparison of nonoral estradiol delivery in postmenopausal women," *Am. J. Obstet. Gynecol.* 159: 1540–6 (1988); Chetkowski, R. J. et al., "Biologic effects of transdermal estradiol," *N. Engl. J. Med.* 314: 1615–20 (1986); Ralston, S. H. et al., "Effect of subdermal estrogen and estrogen/testosterone implants on calcium and phosphorus homeostasis after oophorectomy," *Maturitas* 6: 341–44 (1984)].

Androgens have been administered in these settings to improve sexual functioning, but there are significant negative effects. The administration of even a low dose (e.g., 1.25 to 2.5 mg) of an oral androgen, such as methyltestosterone, with oral estrogens is associated with detrimental changes in blood cholesterol patterns [Notelovitz, M. et al., "Influence of extended treatment with oral estrogens/androgen combination on lipids and lipoproteins in surgically menopausal women," *North American Menopause Society*, 1991, Meeting Abstract S-B5 (Montreal, Canada 1991); Youngs, D. D. & Sherwin, B. B., "Effects of an oral estrogen-androgen preparation on lipoprotein lipids in postmenopausal women: a pilot study," *North American Menopause Society*, 1991, Meeting Abstract P-130 (Montreal, Canada 1991). The addition of testosterone implants to estrogen appears to have only a small impact on cholesterol patterns. While it may negate the positive beneficial effects of the estrogen on cholesterol, a detrimental effect is not clearly seen [Farish, E. et al., "The effects of hormone implants on serum lipoproteins and steroid hormones in bilaterally oophorectomized women," *Acta Endocrinologica* 106: 116–20 (1984)].

The use of pellets of testosterone unfortunately results in large variations in serum levels of testosterone over time. High levels are observed shortly after administration [Burger, H. G. et al, "The management of persistent menopausal symptoms with estradiol-testosterone implants: clinical, lipid and hormonal results," *Maturitas* 6: 351–8 (1984)]. Elevated serum testosterone levels with associated virilization or masculinization can occur with repeated administration, if caution is not used [Urman, B. et al., "Elevated serum testosterone, hirsutism, and virilism associated with combined androgen-estrogen hormone replacement therapy," *Obstet. Gynecol.* 77: 595–8 (1991)]. Further, the serum testosterone levels achieved with such approaches may be substantially above usual levels is normal premenopausal women [Sherwin, B. B. et al., "Postmenopausal estrogen and androgen replacement and lipoprotein lipid concentrations," *Am. J. Obstet. Gynecol.* 156: 414–9 (1987)].

It has generally been assumed that treatment of oophorectomized women with low-dose estrogen, such as 0.625 mg of oral conjugated estrogens, will prevent any loss of bone mineral density (BMD) [Genant, H. et al., "Quantitative computed tomography of vertebral spongiosa: a sensitive method for detecting early bone loss after oophorectomy," *Ann. Intern. Med.* 97: 699–705 (1982)]. Recent clinical studies on women with a medical oophorectomy (induced by a gonadotropin releasing hormone agonist, GnRHA) have clearly shown that this is incorrect, and that a conventional oral dose of 0.625 to 0.9 mg of conjugated estrogens is inadequate. While higher doses of estrogens may be employed to prevent loss of BMD, exogenous estrogen is associated with a significant increase in the risk of breast cancer. This is a dose-dependent effect, so that the lowest possible dose of estrogen to prevent adverse symptoms is desirable.

Preliminary results with the addition of a small dose of oral replacement androgen (1.25 to 2.5 mg of methyltestosterone) to the GnRHA plus conjugated estrogens regimen show protection against the loss of BMD. Unfortunately, the addition of the methyltestosterone has produced detrimental changes in serum cholesterol as noted previously.

It is an object of the present invention to provide methods and formulations which are useful in long-term treatment of oophorectomized women and women with other forms of ovarian failure.

SUMMARY OF THE INVENTION

In accordance with the present invention, there are provided compositions and methods for treating oophorectomized women, wherein an estrogenic composition and an androgenic composition are concurrently administered according to specific protocols as defined herein for long-term, zero-order sustained release. In all protocols an amount of an estrogenic composition effective to prevent symptoms and signs of estrogen deficiency is administered; the symptoms of estrogen deficiency which may develop after oophorectomy include, but not are not limited to, symptoms of the menopause, vasomotor instability, harmful alterations in serum cholesterol or its fractions, and urogenital atrophy. An androgenic composition is concurrently administered in conjunction with the administration of the estrogenic composition. The androgenic composition is administered in an amount effective to increase a patient's effective androgen level to a level not exceeding normal premenopausal levels, and in particular in concert with the estrogenic composition to maintain BMD. Use of delivery systems for long-term release of estrogens and androgens, requiring infrequent administration, makes the inventive regimens both practical and potentially more effective in preventing the symptoms and signs attendant to an oophorectomy or ovarian failure.

DETAILED DESCRIPTION OF THE INVENTION

Pursuant to the present invention, the regimen comprises a slow-release (or depot) formulation which is effective for an extended period of time. Depending on the composition and mode of administration, the inventive formulation may be effective for as short a period as 3 days to as long as six months or more; extended-use formulations may be effective for as long as five years or more. It is presently preferred that the formulation be effective over about a three or four month period.

Many of the side effects of oophorectomy reflect the hypoestrogenic state and can thus be prevented in accordance with the present invention by add-back estrogen therapy. Accordingly, in accordance with the present invention an effective amount of an estrogenic composition is administered to prevent symptoms and signs of estrogen deficiency.

As the add-back estrogen, a single-component natural or synthetic estrogen composition or a combination of such compositions can be used to maintain a constant systemic level. A substantial body of information exists concerning the effects of hormone replacement therapy after a natural or surgical menopause. Although more is known about the effects of conjugated equine estrogens (CEE) as estrogen replacement therapy (ERT) than any other agent, it is presently preferred that a single-component or two-component composition be employed.

As used herein, estrogenic compositions refer to both the natural and the synthetic materials. These materials are well known in the art. Natural and synthetic estrogenic compositions which can be used according to the invention described herein include natural estrogenic hormones and congeners, including, but not limited to, estradiol, estradiol benzoate, estradiol cypionate, estradiol valerate, estrone, diethylstilbestrol, piperazine estrone sulfate, ethinyl estradiol, mestranol, polyestradiol phosphate, estriol, estriol hemisuccinate, quinestrol, estropipate, pinestrol and estrone potassium sulfate. Equine estrogens, such as equilelinin, equilelinin sulfate and estetrol, may also be employed.

Typical dose ranges for estrogenic compositions depend not only upon the choice of composition, but also upon the characteristics of the patient. For an adult human female patient administered estradiol, typical dose ranges are such that the serum level of estradiol is maintained at a level of about 15 to about 50 pg/ml. Most preferably, the serum level of estradiol is about 20 to about 35 pg/ml. These levels are significantly lower than the serum levels achieved in accordance with the ERT regimens in current use which are known to maintain normal bone density. By the term "estradiol equivalents" as used herein is meant the amount of an estrogenic composition that provides a biological effect equivalent to administration of a specified amount of estradiol. As described in some detail hereinafter, the estrogenic composition is administered in a suitable formulation for maintaining a sustained zero-order release, so as to achieve a continuous replacement of a sufficient level of estrogen over the entire period of administration to minimize or eliminate the symptoms and signs of estrogen deficiency.

Concurrent with administration of an estrogenic composition, an androgenic composition is administered in an amount to increase a patient's effective androgen level to a level not exceeding normal premenopausal level, and in particular in concert with the estrogenic composition to maintain BMD. Administration to oophorectomized women of the androgen methyltestosterone has been shown to add significantly to the bone effects of ERT [Watts, N. et al., "Effects of oral esterified estrogens and esterified estrogens plus androgens on bone mineral density in postmenopausal women," *North American Menopause Society*, Meeting Abstract S-F16 (Montreal, Canada 1991)]. Restoration of a patient's effective normal androgen levels is desirable, as oophorectomy has the effect of reducing effective serum androgen levels, in some cases significantly. For purposes of the present invention, normal androgen levels are on the order of about 20 to about 80 ng/dl for testosterone.

Suitable androgenic hormones for use in accordance with the present invention include, but are not limited to, testosterone, androstenedione, dihydrotestosterone, testosterone propionate, testosterone enanthate, testosterone cypionate, methyltestosterone, danazol, dromostanolone propionate, ethylestrenol, methandriol, nandrolone decanoate, nandrolone phenpropionate, oxandrolone, oxymethalone, stanozolol and testolactone. Typical dose ranges for androgenic hormones depend upon the choice of composition and the individual patient. For an adult human female administered testosterone, typical doses are administered to provide serum levels of testosterone of from about 20 ng/dl to about 80 ng/dl, and preferably about 40 to about 60 ng/dl; with other androgenic hormones, the amount to be administered is such as to provide the effective equivalent of the above-noted serum levels of testosterone.

In accordance with the present invention, the delivery vehicle of the invention provides for administration of estrogenic composition and androgenic composition by a subcutaneous, intramuscular, vaginal or transdermal route. The carrier vehicle or device for each component is selected from a wide variety of materials and devices which are already known per se or may hereafter be developed which provide for controlled release of the compositions in the particular physiological environment. In particular, the carrier vehicle of the delivery system is selected such that near zero-order release of the components of the regimen is achieved. In the context of the present invention, the carrier vehicle should therefore also be construed to embrace particular formulations of the compositions which are themselves suitable for providing near zero-order release. A targeted steady-state release can be obtained by suitable adjustment of the design or composition of the delivery system. Known devices suitable for use as a delivery system in accordance with the present invention include, for example, drug-delivery pump devices providing near zero-order release of the components of the regimen.

One suitable formulation to achieve the desired near zero-order release of the components comprises injectable microcapsules or microspheres prepared from a biodegradable polymer, such as poly(dl-lactide), poly(dl-lactide-co-glycolide), polycaprolactone, polyglycolide, polylactic acid-co-glycolide, poly(hydroxybutyric acid), a polyortho-ester or a polyacetal. Injectable systems comprising microcapsules or microspheres of a diameter on the order of about 50 to about 500 μm offer advantages over other delivery systems. For example, they generally use less hormone and may be administered by paramedical personnel. Moreover, such systems are inherently flexible in the design of the duration and rate of separate drug release by selection of microcapsule or microsphere size, drug loading and dosage administered. In addition, such microcapsules or microspheres can be successfully sterilized with gamma irradiation.

Microcapsules or microspheres are systems comprising a polymeric wall that encloses a liquid or solid core. The capsule wall usually does not react with the core material; however, it is designed to provide sufficient strength to enable normal handling without rupture while being sufficiently thin to allow a high core to wall volume ratio. The capsule contents remain within the wall until released by diffusion or other means that dissolve, melt, break, rupture or remove the capsule material. Preferably, the capsule wall can be made to degrade and decompose in suitable environments while diffusing the core material through the capsule wall to allow for its slow, prolonged delivery. The mechanism of release in biodegradable microcapsules is a combination of drug diffusion and polymer biodegradation. Therefore, the rate and duration of release are determined by microcapsule size, drug content and quality, and polymer parameters, such as crystallinity, molecular weight and composition. In particular, adjustment in the amount of drug released is generally achieved by modification of capsule wall thickness, capsule diameter, and/or polymer composition.

Detailed information concerning the design and use of microspheres and microcapsules is provided by, e.g., Lewis, D. H., "Controlled release of bioactive agents from lactide/glycolide polymers," in Chasin, M. & Langer, R. (eds.), *Biodegradable Polymers as Drug Delivery Systems*, pp. 1–41 (1990), the entire disclosure of which is hereby incorporated by reference. Several methods are currently available for preparing microcapsules or microspheres. As discussed in Nuwayser, E. S. et al., "Microencapsulation of contraceptive steroids," in Zatuchni, G. L. et al. (eds.), *Long-acting Contraceptive Delivery Systems*, pp. 64–76 (1984), the entire disclosure of which is hereby incorporated by reference, most of these methods can be classified under three major categories: coacervation, coagulation and air-suspension coating.

An exemplary material for use in the formulation of suitable microcapsules or microspheres is poly(dl-lactide-co-glycolide) as described in Lewis, D. H. & Tice, T. R., "Polymeric considerations in the design of microencapsulation of contraceptive steroids," in Zatuchni, G. L. et al. (eds.), *Long-acting Contraceptive Delivery Systems*, pp. 77–95 (1984), the entire disclosure of which is hereby incorporated by reference. The solvent evaporation process described therein is suitable for preparing microcapsules or microspheres in a size range acceptable for administration by conventional syringe and needle; moreover, the yield or fraction of microcapsules or microspheres within a desired size range can be selected and achieved with appropriate process adjustments. This enables the preparation of diffusional controlled-release formulations in which the duration of drug release is directly related to total surface area or particle size. Another exemplary material is poly(ε-caprolactone) as described in Pitt, C. G. & Schindler, A., "Capronor—A biodegradable delivery system for levonorgestrel," in Zatuchni, G. L. et al. (eds.), *Long-acting Contraceptive Delivery Systems*, pp. 48–63 (1984), the entire disclosure of which is hereby incorporated by reference. Other biodegradable polymeric materials suitable for preparation of microcapsules for controlled (i.e., near zero-order) release would be readily determined through routine experimentation by those skilled in the art.

An alternative delivery system suitable for use in accordance with the present invention comprises fibers or filaments comprising the active agents and biodegradable or non-biodegradable polymers. Precision delivery systems can be mass-produced by this method; moreover, geometrically configured controlled-release devices can be produced by, e.g., wrapping drug-releasing fibers around conventional intravaginal rings or other intravaginal devices. Typically, fibrous delivery systems rely on membrane-moderated diffusion mechanisms to control the rate and duration of drug release. Monolithic drug-releasing fibers may be prepared by conventional spinning processes; when reservoir-type fibrous systems are desired, either a fast-releasing monolithic fiber is prepared and then coated with a rate-controlling sheath, or a coaxial spinning process is employed, in which the drug is extruded as the core of the fiber at the same time as the rate-controlling polymer sheath. Suitable fibers for providing zero-order release of the active agents and methods for the preparation thereof are described in Cowsar, D. E. & Dunn, R. L., "Biodegradable and nonbiodegradable fibrous delivery systems," in Zatuchni, G. L. et al. (eds.), *Long-acting Contraceptive Delivery Systems*, pp. 145–163 (1984), the entire disclosure of which is hereby incorporated by reference.

Other suitable materials for preparation of such devices include silicon-based materials, such as polydimethylsiloxanes, which have been employed to prepare capsule-type, matrix-type and microsealed drug delivery systems. For example, a suitable device may be prepared by coating a non-medicated silicone rubber core with a thin layer of silicone rubber (such as MDX-4-4210 Clean Grade Elastomer, available from Dow Corning) which contains micronized crystalline forms of the active agents. An implant of this type (for administration of estradiol) is described in Ferguson, T. H. et al., "Compudose: an implant system for growth promotion and feed efficiency in cattle," *J. Controlled Release* 8, 45–54 (1988), the entire disclosure of which is hereby incorporated by reference. Improved matrix release devices may be prepared by incorporating water-soluble carriers, such as sodium alginate, or by using additives, such as co-solvents or salts, which enhance the release rate of active agents from the polymer matrix.

In general, contraceptive vaginal rings may be designed as homogeneous mixtures of composition and silastic; as a core vaginal ring surrounded by silastic; as a shell ring with a core of silastic, surrounded by a layer of composition and silastic covered by a tube of silastic; as a band ring of inert silastic with a drug-containing band on the ring; or as a combination of the various designs to permit the specific release characteristics desired. In this regard, useful systems are described in the following: Jackanicz, T. M., "Vaginal ring steroid-releasing systems," pp. 201–12; Diczfalusy, E. & Landgren, B. -M., "Some pharmacokinetic and pharmacodynamic properties of vaginal delivery systems that release small amounts of progestogens at a near zero-order rate," pp. 213–27; and Roy, S. & Mishell, Jr., D. R., "Vaginal ring clinical studies: update," pp. 581–94: all in Zatuchni, G. L. et al. (eds.), *Long-acting Contraceptive Delivery Systems* (1984), the entire disclosures of which are hereby incorporated by reference.

For transdermal delivery of the active agents, suitable pads or bandages are also well known in the art. Typically, these pads comprise a backing member defining one exterior surface, a surface of pressure-sensitive adhesive defining a second exterior surface, and disposed therebetween a reservoir containing the active agents confined therein. Suitable transdermal delivery systems are disclosed in U.S. Pat. Nos. 3,731,683 and 3,797,494 to Zaffaroni and U.S. Pat. No. 4,336,243 to Sanvordeker et al., the entire disclosures of which are hereby incorporated by reference.

The inventive regimen is designed to reduce the degree of adverse effects associated with oophorectomy. In particular, oophorectomy has been recognized as having an adverse impact on bone metabolism. BMD is known to fall after an oophorectomy; the fall is most evident in regions of trabecular bone. This loss of BMD is secondary to the reduction in estrogens and androgens. In accordance with the present invention, estrogen combined with an androgen is administered to reduce BMD loss in oophorectomized women. The ability of estrogen to control hot flashes and other menopausal symptoms is well documented. By combining appropriate levels of estrogen and androgen replacement therapy, the effects of the hypoestrogenic and hypoandrogenic state induced by the oophorectomy are prevented.

A particularly significant advantage of the administration of androgens in accordance with the present invention is to enable a reduction in the dose of estrogen necessary to prevent loss of BMD. As previously noted, to minimize the potential increase in risk of breast cancer, the lowest possible dose of exogenous estrogen is clearly desirable.

An increased risk of cardiovascular disease has been a further concern in oophorectomized women. According to the present invention, add-back estrogen is employed in an amount which is sufficient to reduce any increased risk of cardiovascular disease. One reason for this reduction in risk of cardiovascular disease is likely to be the beneficial effects of estrogen on serum cholesterol. Add-back estrogen at a level as proposed herein is predicted to result in a beneficial rise in high density lipoprotein cholesterol (HDLC) and a beneficial fall in low density lipoprotein cholesterol (LDLC), a clearly beneficial overall effect. The androgen replacement at a level as proposed herein may slightly increase LDLC and slightly decrease HDLC, but the overall predicted effect of the proposed regimen remains beneficial.

While estrogen thus has significant positive effects, it is nonetheless important to select appropriate levels of estrogenic and androgenic compositions so as to achieve an appropriate balance between the clear advantages achieved and the potential risks inherent in such treatment. Unlike the heretofore known protocols, the present invention calls for administration of amounts of estrogenic and androgenic compositions which in concert achieve the desired effects without the adverse consequences of administering excess amounts of estrogens and/or androgens. Therefore, the androgenic composition is administered in an amount to increase a patient's effective androgen level to a level not exceeding normal premenopausal levels so as to avoid complications associated with excess androgen levels in women, such as hirsutism. Similarly, the estrogenic composition is administered in the lowest amount effective to prevent symptoms and signs of estrogen deficiency, so as to minimize risks associated with higher levels of estrogenic compositions, such as increased risk of breast cancer.

In addition, by maintaining zero-order administration of estrogens and androgens, in accordance with the present invention it is possible to achieve the desired effects with the minimum total doses of both agents. Unlike earlier protocols, in accordance with the present invention at no time will there be excess estrogen or androgen present.

The following example will serve to illustrate the invention without in any way being limiting thereon.

EXAMPLE

This example describes a delivery system for intramuscular administration over a 4-month duration. The delivery system administers a natural estrogenic steroid (estradiol) and a natural androgenic steroid (testosterone). The serum level of estradiol is maintained at about 40 pg/ml by provision of 5 mg thereof in the form of microspheres prepared from a copolymer of lactide and glycolide; as is well known in the art, this copolymer provides for an effective time-release formulation which is biodegradable. Androgen is provided in a dose of 24 mg of testosterone, also in the form of microspheres prepared from a copolymer of lactide and glycolide, so as to maintain serum levels of testosterone at about 50 ng/dl.

While there have been shown and described the fundamental novel features of the invention, it will be understood that various omissions, substitutions and changes in the form and details of the devices illustrated may be made by those skilled in the art without departing from the spirit of the invention. It is the intention, therefore, to be limited only as indicated by the scope of the following claims.

What is claimed is:

1. A composition for preventing symptoms and signs of loss of ovarian function in oophorectomized women over a period of time consisting essentially of:

a slow-release formulation of an estrogenic composition which maintains serum level of said estrogenic composition over said period of time at a level effective to prevent symptoms and signs of estrogen deficiency, wherein said serum level of said estrogenic composition is equivalent to serum estradiol levels in the range of about 15 to about 50 pg/ml; and a slow-release formulation of an androgenic hormone which increases serum level of said androgenic hormone over said period of time to a level not exceeding a normal premenopausal level for a patient, wherein said serum level of said androgenic composition is equivalent to serum testosterone levels in the range of about 20 to about 80 ng/dl.

2. A composition according to claim 1, wherein said estrogenic composition is selected from the group consisting of estradiol, estradiol benzoate, estradiol cypionate, estradiol valerate, estrone, diethylstilbestrol, piperazine estrone sulfate, ethinyl estradiol, mestranol, polyestradiol phosphate, estriol, estriol hemisuccinate, quinestrol, estropipate, pinestrol, estrone potassium sulfate, equilelinin, equilelinin sulfate, estetrol and mixtures of two or more thereof.

3. A composition according to claim 1, wherein said androgenic hormone is selected from the group consisting of testosterone, androstenedione, dihydrotestosterone, testosterone propionate, testosterone enanthate, testosterone cypionate, methyltestosterone, danazol, dromostanolone propionate, ethylestrenol, methandriol, nandrolone decanoate, nandrolone phenpropionate, oxandrolone, oxymethalone, stanozolol and testolactone.

4. A composition according to claim 1, wherein said period of time is about 3 days to about five years.

5. A composition according to claim 4, wherein said period of time is about three months to about four months.

6. A composition according to claim 1, for administration by a subcutaneous, intramuscular, vaginal or transdermal route.

7. A composition according to claim 1, in the form of an implantable device.

8. A composition according to claim 1, wherein said serum level of said estrogenic composition is equivalent to serum estradiol levels in the range of about 20 to about 35 pg/ml.

9. A method for preventing symptoms and signs of loss of ovarian function in oophorectomized women over a period of time, comprising:

administering an estrogenic composition in an amount effective to maintain serum level of said estrogenic composition over said period of time at a level effective to prevent symptoms and signs of estrogen deficiency, said serum level of said estrogenic composition being equivalent to serum estradiol levels in the range of about 15 to about 50 pg/ml; and simultaneously administering an androgenic composition over said period of time in an amount effective to increase effective androgen level to a level not exceeding a normal premenopausal level for a patient, wherein said serum level of said androgenic composition is equivalent to serum testosterone levels in the range of about 20 to about 80 ng/dl.

10. A method according to claim 9, wherein said period of time is about 3 days to about five years.

11. A method according to claim 10, wherein said period of time is about three months to about four months.

12. A method according to claim 9, wherein said estrogenic composition is selected from the group consisting of estradiol, estradiol benzoate, estradiol cypionate, estradiol valerate, estrone, diethylstilbestrol, piperazine estrone sulfate, ethinyl estradiol, mestranol, polyestradiol phosphate, estriol, estriol hemisuccinate, quinestrol, estropipate, pinestrol, estrone potassium sulfate, equilelinin, equilelinin sulfate, estetrol and mixtures of two or more thereof.

13. A method according to claim 9, wherein said androgenic hormone is selected from the group consisting of testosterone, androstenedione, dihydrotestosterone, testosterone propionate, testosterone enanthate, testosterone cypionate, methyltestosterone, danazol, dromostanolone propionate, ethylestrenol, methandriol, nandrolone decanoate, nandrolone phenpropionate, oxandrolone, oxymethalone, stanozolol and testolactone.

14. A method according to claim 9, wherein said serum level of said estrogenic composition is equivalent to serum estradiol levels in the range of about 20 to about 35 pg/ml.

* * * * *